US012594065B2

(12) United States Patent
Biedermann et al.

(10) Patent No.: US 12,594,065 B2
(45) Date of Patent: Apr. 7, 2026

(54) INSTRUMENT FOR USE IN SURGERY

(71) Applicant: BIEDERMANN TECHNOLOGIES GMBH & CO.KG, Donaueschingen (DE)

(72) Inventors: Timo Biedermann, Trossingen (DE); Markku Biedermann, Key Biscayne, FL (US); Achim Schünemann, Villingen-Schwenningen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 829 days.

(21) Appl. No.: 17/739,703

(22) Filed: May 9, 2022

(65) Prior Publication Data

US 2022/0361866 A1 Nov. 17, 2022

Related U.S. Application Data

(60) Provisional application No. 63/187,546, filed on May 12, 2021.

(30) Foreign Application Priority Data

May 12, 2021 (EP) ..................................... 21173686

(51) Int. Cl.
| | |
|---|---|
| *A61B 17/70* | (2006.01) |
| *A61B 17/04* | (2006.01) |
| *A61B 17/29* | (2006.01) |

(52) U.S. Cl.
CPC ...... *A61B 17/0401* (2013.01); *A61B 17/0469* (2013.01); *A61B 17/0482* (2013.01); *A61B 17/7082* (2013.01); *A61B 2017/2929* (2013.01)

(58) Field of Classification Search
CPC .................................................. A61B 17/7082
See application file for complete search history.

(56) References Cited

U.S. PATENT DOCUMENTS

| | | | |
|---|---|---|---|
| 10,105,165 B2 | 10/2018 | Biedermann et al. | |
| 10,433,883 B2 * | 10/2019 | DiVincenzo | ....... A61B 17/1604 |

(Continued)

FOREIGN PATENT DOCUMENTS

| | | |
|---|---|---|
| CN | 111329572 A | 6/2020 |
| WO | WO 2019/002992 A1 | 1/2019 |

OTHER PUBLICATIONS

European Search Report for Application No. 21173686.3, mailed Nov. 9, 2021, 8 pages.

*Primary Examiner* — Nicholas W Woodall
(74) *Attorney, Agent, or Firm* — Womble Bond Dickinson (US) LLP

(57) ABSTRACT

A surgical instrument is connectable to a bone anchor insertion device having a drive shaft that defines a coaxial channel for receiving a needle therethrough. The instrument includes a handle portion configured to be coupled to the drive shaft in a rotationally fixed manner to transmit torque to the drive shaft, a needle holder configured to hold a needle and movable axially relative to the handle portion, an actuator rotatable relative to the handle portion, and a transmission member connectable to the needle holder and movable axially relative to the actuator and comprising a first advancement surface engageable with a second advancement surface of the handle portion to convert rotational movement of the actuator into axial movement of the needle holder relative to the handle portion for axially advancing and retracting a needle held by the needle holder relative to the handle portion.

21 Claims, 12 Drawing Sheets

(56)                    References Cited

U.S. PATENT DOCUMENTS

| | | | | |
|---|---|---|---|---|
| 10,973,558 | B2 | 4/2021 | Kam et al. | |
| 2009/0275994 | A1* | 11/2009 | Phan | B25B 23/101 |
| | | | | 606/103 |
| 2014/0276892 | A1* | 9/2014 | Pakzaban | A61B 17/8875 |
| | | | | 606/104 |
| 2014/0276894 | A1* | 9/2014 | Ramsay | A61B 17/8897 |
| | | | | 606/104 |
| 2016/0030100 | A1* | 2/2016 | Divincenzo | A61B 17/7091 |
| | | | | 606/104 |
| 2018/0132920 | A1* | 5/2018 | Vikinsky | A61B 17/888 |
| 2018/0353224 | A1* | 12/2018 | Kam | A61B 17/7082 |
| 2019/0125421 | A1 | 5/2019 | Smith et al. | |
| 2020/0093530 | A1 | 3/2020 | Klausman et al. | |
| 2020/0100817 | A1* | 4/2020 | DiVincenzo | A61B 17/1604 |
| 2020/0305944 | A1* | 10/2020 | Geist | A61B 17/8872 |
| 2021/0059692 | A1* | 3/2021 | Cha | A61B 17/1655 |
| 2022/0008109 | A1* | 1/2022 | Kaito | A61B 17/7077 |

* cited by examiner

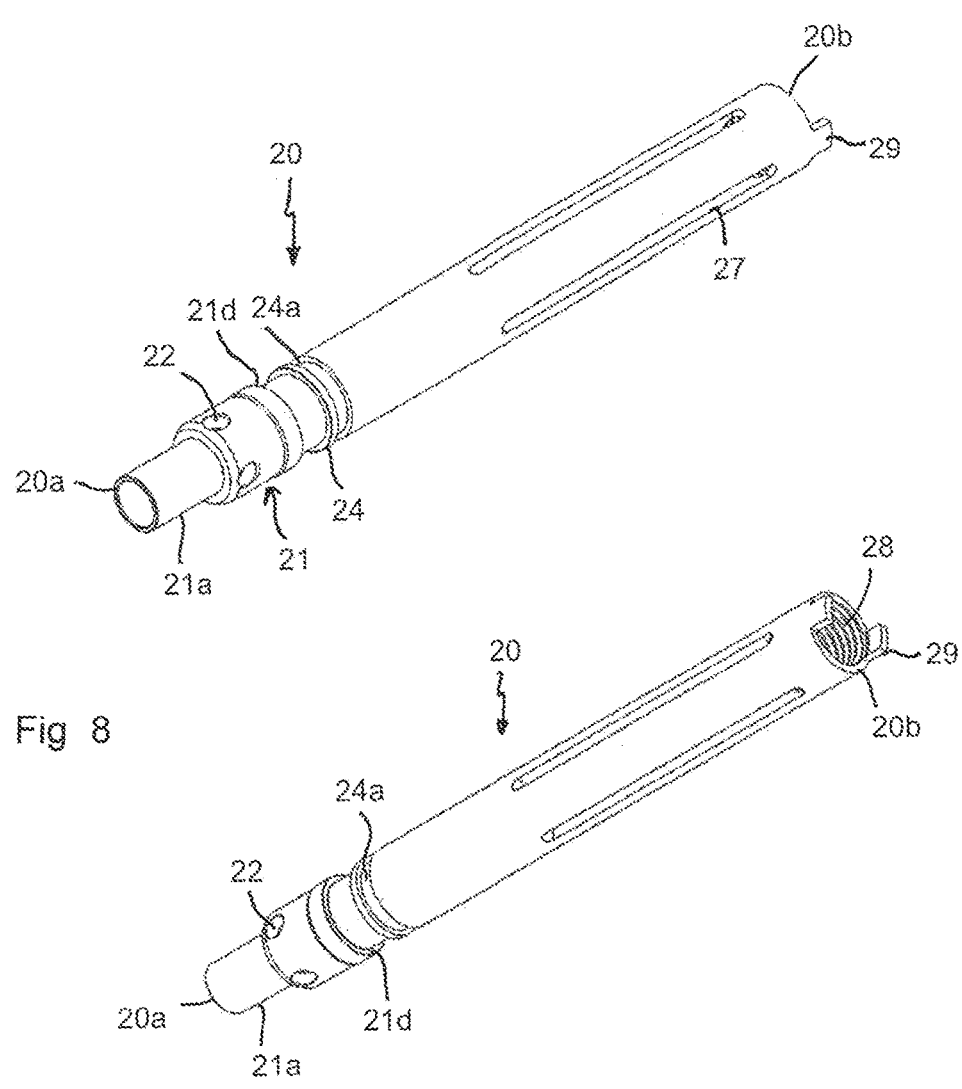
Fig 8
Fig. 9
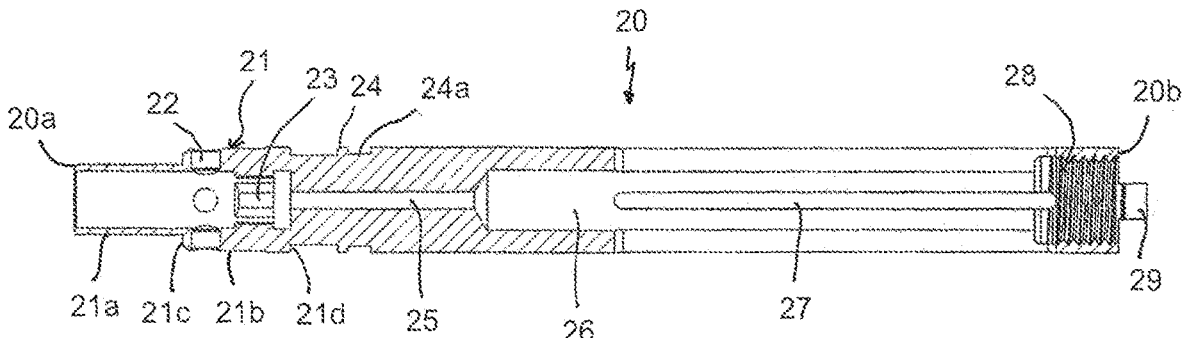
Fig. 10

INSTRUMENT FOR USE IN SURGERY

CROSS-REFERENCE TO RELATED APPLICATION(S)

The present application claims priority to and the benefit of U.S. Provisional Patent Application No. 63/187,546, filed May 12, 2021, the contents of which are hereby incorporated by reference in their entirety, and claims priority from European Patent Application EP 21 173 686.3, filed May 12, 2021, the contents of which are hereby incorporated by reference in their entirety.

BACKGROUND

Field

The application relates to an instrument for use in surgery in connection with a bone anchor insertion device. With the instrument, a position of a needle relative to a bone anchor can be adjusted. Further, the invention relates to a combined surgical instrument including the bone anchor insertion device and the instrument. The surgical instrument may be particularly applicable in musculoskeletal surgery, and in particular, in spinal surgery.

Description of Related Art

In surgery of the spine, a known technique involves the use of Jamshidi needles for inserting Kirschner wires (K-wires), which may be used for the placement of bone anchors such as pedicle screws. According to the known method, first, a small incision is made in the skin of the patient. Then, a Jamshidi needle including a tiny awl is advanced through the incision to the bone. A bore is prepared by hammering and turning the Jamshidi needle back and forth, and then the awl is removed. Subsequently, a K-wire is placed into the hole and the Jamshidi needle is removed. A thread cutter is guided by the K-wire to the hole, and a thread is cut with the thread cutter. After cutting the thread, the thread cutter is screwed back. Finally, a cannulated bone screw is guided by the K-wire to and screwed into the threaded hole. As a last step, the K-wire is removed. In sum, these steps require the use of several instruments and several instrument passes, and may be time consuming, especially in cases where many threaded bores have to be prepared.

A bone anchor insertion device for holding and inserting a bone anchor into the bone, in particular for use with a pedicle screw, is known, for example, from U.S. Pat. No. 10,105,165 B2. The bone anchor insertion device includes a holding member with a seat for holding the head of the bone anchor, the holding member having two arms that are configured to encompass the head of the bone anchor, and a drive shaft for engaging the head of the bone anchor to screw the bone anchor into bone, and a displacement member acting onto the holding member such that the holding member can assume a first configuration in which the head can enter the seat and a second configuration in which the head is held in the seat and the shank of the bone anchor can be screwed into bone.

U.S. Pat. No. 10,433,883 B2 describes surgical instruments for delivering bone anchor assemblies into bone. Use of these assemblies can eliminate one or more of the steps in a conventional bone anchor installation procedure. The surgical instrument includes a handle assembly having an elongate shaft extending distally therefrom. The handle assembly can be configured to axially translate a carrier assembly that secures a stylet extending therethrough. Translation of the stylet can be made relative to a distal end of the elongate shaft.

SUMMARY

It is an object of the invention to provide an improved instrument, which allows for the reduction of surgical steps and the carrying out of certain surgical steps more efficiently.

An embodiment of the instrument for use in surgery that is configured to be used with a bone anchor insertion device includes a handle portion configured to be coupled to a drive shaft of the bone anchor insertion device to transmit torque to the drive shaft, a needle holder configured to receive a needle and that is movable with respect to the handle portion, an actuator rotatable with respect to the handle portion and a transmission member configured to be coupled to the needle holder and to convert a rotational movement of the actuator into a translational movement of the needle holder. Thereby, it may be possible to advance and retract the needle to adjust a position of a tip of the needle relative to the shank of the bone anchor. The transmission member has a first advancement structure that is configured to engage a second advancement structure provided at the handle portion for effecting the translational movement of the needle holder.

The instrument according to an embodiment may be coupled to any bone insertion device, also called a shank inserter, which includes a drive shaft to engage and rotate a bone anchor with a threaded shank into bone. Such a shank inserter may have a standard coupling at a rear end of the drive shaft, for example, a ¼ inch square connection portion, that can be coupled to the instrument via a standard coupling used for ¼ inch connection portions. Hence the instrument can form a part of a modular system and can preferably be selectively coupled to different shank inserters. Moreover, the instrument may be used together with an adapter that carries, for example, a navigation instrument for computer aided imaging and/or navigation.

With the instrument according to an embodiment of the invention, a maximum length of translation of a tip of a needle which is to be used during insertion of the bone anchor is defined by the length of the handle portion which houses a hollow shaft therein in which the needle holder can travel back and forth. Such a maximum length may be, for example, around 50 mm to 70 mm. Thus, with the instrument, a needle of a fixed length may be used together with bone anchors having different shank lengths. It may also be possible to use the instrument with needles of different types and/or with needles of different lengths. Nevertheless the instrument is compact, as a cavity formed in the handle portion that drives the drive shaft of the shank inserter is used as a path of translation of the needle holder.

The position of the tip of the needle in the axial direction relative to the tip of the bone anchor can be adjusted in a stepless manner. Once a position of the needle has been adjusted, this position can be maintained and the shank of the bone anchor can be screwed into the bone. Removal and/or exchange of the needle, if necessary, can be carried out in a simple and time efficient manner.

With the instrument according to an embodiment of the invention, various techniques for anchoring the bone anchor in bone may be realized. In particular, the instrument may be used in minimally invasive surgery (MIS), and preferably using bone anchors with a self-cutting thread.

An embodiment of a method of use includes at least the steps of connecting the instrument to a drive shaft of an instrument for inserting a bone anchor into bone before or after connecting a cannulated bone anchor to the drive shaft, inserting a needle into the instrument and fixing the needle, translating the needle via the actuator such that a tip of the needle extends out of the tip of the bone anchor to a desired distance, inserting the needle into bone, preferably further translating the needle relative to the bone anchor to a desired depth, and inserting the bone anchor along the needle by rotating the handle portion. Afterwards, the needle may be removed from the bone anchor before removing the shank inserter with the instrument, or simultaneously therewith.

BRIEF DESCRIPTION OF THE DRAWINGS

Further features and advantages of the invention will become apparent from the description of embodiments by means of the accompanying drawings. In the drawings:

FIG. 8 shows a perspective view from a front end of a hollow shaft of the instrument of FIGS. 3 to 7.

FIG. 9 shows a perspective view from a rear end of the hollow shaft of FIG. 8.

FIG. 10 shows a cross-sectional view of the hollow shaft of FIGS. 8 and 9, the cross-section taken in a plane including a central longitudinal axis of the hollow shaft.

DETAILED DESCRIPTION

Figure 1:
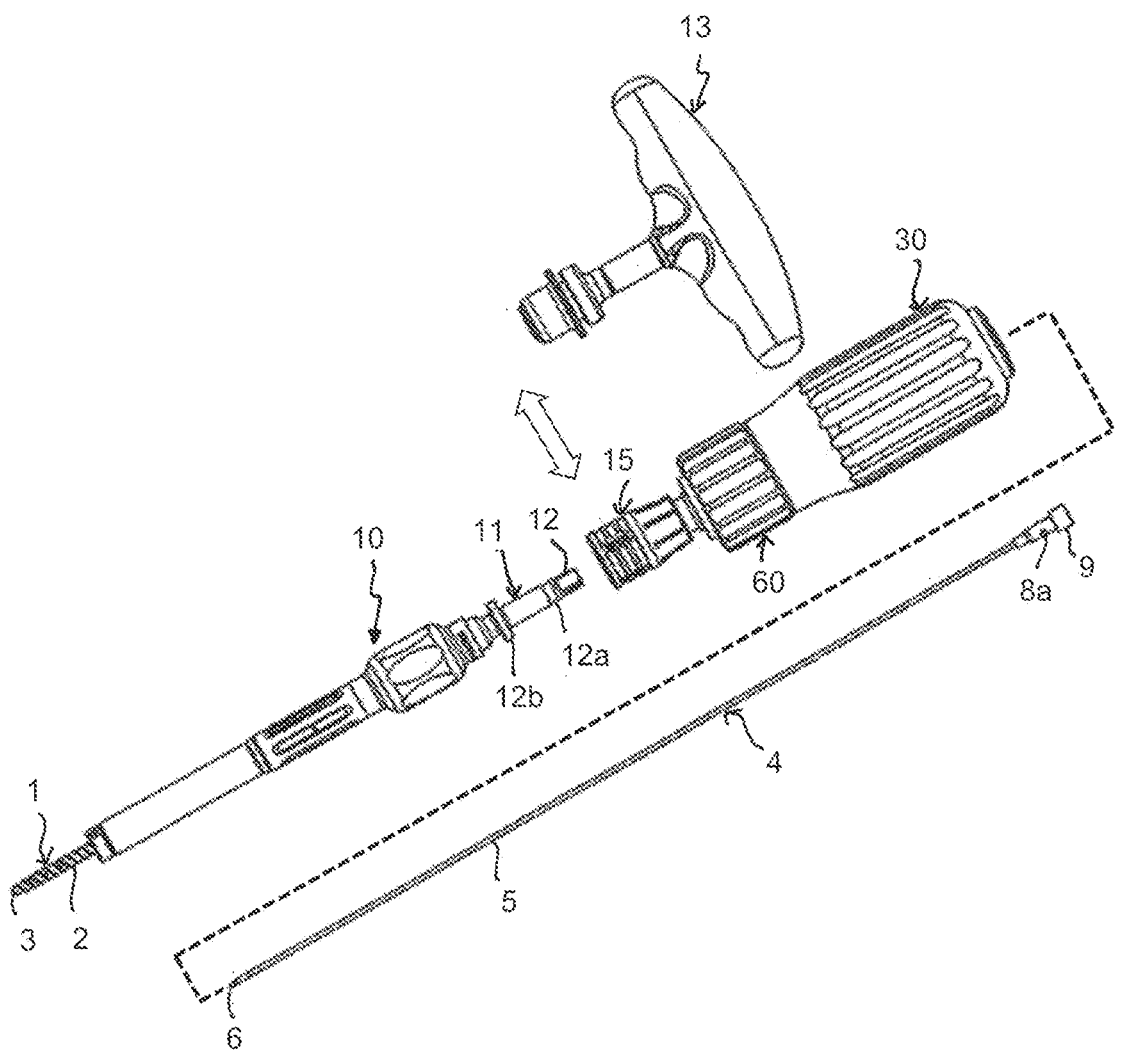
FIG. 1 shows a perspective exploded view of an embodiment of an instrument and a device for inserting a bone anchor.
Figure 2:
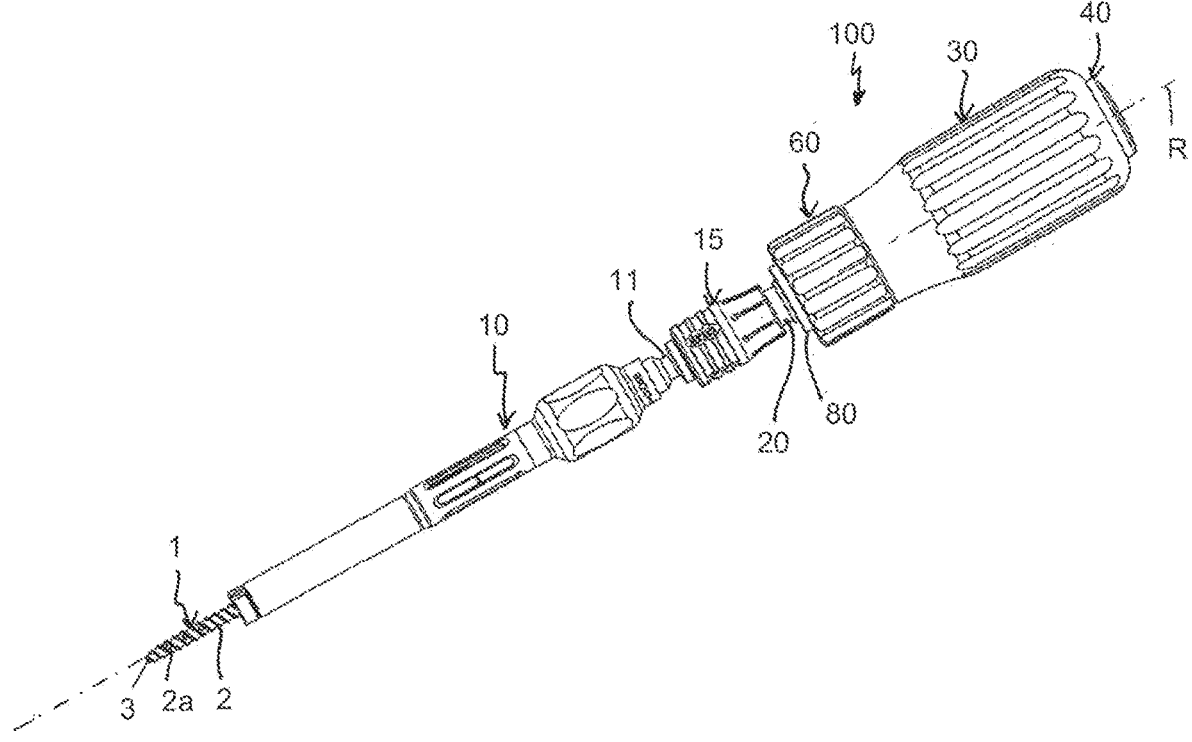
FIG. 2 shows a perspective view of the instrument and the device for inserting a bone anchor of FIG. 1 in an assembled state.

Referring to FIGS. 1 and 2, a surgical instrument in the form of a shank inserter 10 is configured to insert a bone anchor 1 into bone. The bone anchor 1 usually has a threaded shank 2 with a tip 3, and may also have a head (not shown) at an end of the shank 2 opposite to the tip 3. A needle 4 may be used to place the bone anchor 1 at a desired position on the bone surface and to prepare a tiny hole in the bone that defines an insertion path for the bone anchor 1. For this purpose, the bone anchor 1 may be cannulated so that the needle 4 can extend through the bone anchor 1 from the head to the tip 3. Optionally, the shank 2 may have lateral openings 2a to allow bone cement or another substance to be introduced and exit therethrough. The shank inserter 10 may be any known bone anchor insertion device. Such a shank inserter 10 is configured to engage the bone anchor 1, usually at the head, with a front end of a drive shaft 11, and to connect the bone anchor 1 to the drive shaft 11 so that torque can be transmitted via the drive shaft 11 to the shank 2 to screw the shank 2 into the bone. The drive shaft 11 has a connection portion 12 at its rear end that is shaped and sized to permit quick connection to and release from other instrument parts, such as a T-handle 13 or another type of handle or adapter. The connection portion 12 in the embodiment may be designed as a male connection portion with a polygon outer contour, such as a square-end. In a specific embodiment, the connection portion may be a ¼ inch connection portion used in many standard couplings. Adjacent to or at a small distance from the connection portion 12, there may be a groove 12a engageable by one or more holding structures or members for preventing axial movement of the drive shaft 11 when the drive shaft 11 is connected to other instrument parts. Moreover, a projection 12b may serve as an abutment for the connection to other instrument parts. To allow the use of the needle 4, the drive shaft 11 is cannulated. This permits the needle 4 to extend completely through the drive shaft 11 and through the bone anchor 1.

It shall be noted that the shank inserter may also only include a drive shaft without other holding or counter holding features that engage the bone anchor.

Referring further to FIGS. 3 to 7, an instrument 100 for use with a surgical instrument such as the shank inserter 10, can be coupled via a coupling portion 15 to the shank inserter 10, more specifically to the drive shaft 11 of the shank inserter 10. The coupling portion may optionally be part of the instrument. The instrument 100 includes a hollow shaft 20 that is configured to be connected via the coupling portion 15 to the drive shaft 11 of the shank inserter 10, and that is further configured to be connected to a handle portion 30. The handle portion 30 can be rotated by a user, whereby the torque is transmitted onto the hollow shaft 20, and as a result onto the drive shaft 11 of the shank inserter 10. A fixation member 40 may be used to connect the hollow shaft 20 with the handle portion 30 in a rotationally and translationally fixed manner. Moreover, the hollow shaft 20 is housed at least partially in a cavity of the handle portion 30. A needle holder 50 is configured to be arranged in the hollow shaft 20. The needle holder 50 can be translated within the hollow shaft 20 via an actuating mechanism to permit a tip 6 of the needle 4 to be advanced and retracted relative to the tip 3 of the shank 2 of the bone anchor 1.

The actuating mechanism includes an actuator 60 and a transmission member 70. The actuator 60 is rotatable relative to the handle portion 30, and therefore also relative to the drive shaft 11 of the shank inserter 10. The transmission member 70 is guided by the actuator 60 in a manner such that when the actuator is rotated, the transmission member 70 follows the rotational movement of the actuator, and at the same time advances axially relative to the handle portion 30. In addition, the transmission member 70 is connected to the needle holder 50 in a manner such that the needle holder follows the axial advancement of the transmission member 70. Thus, the transmission member 70 is configured to convert a rotational movement of the actuator 60 into a translational movement of the needle holder 50. By means of this, the needle 4 can be advanced and retracted relative to the bone anchor 1 independently from a position of the bone anchor 1.

An axis of rotation R of the instrument 100, which is also a central longitudinal axis of parts of the instrument, is coaxial with an axis of rotation of the shank inserter 10 and the screw axis of the bone anchor 1.

In the following, the parts of the instrument 100 will be explained in greater detail.

Figure 3:
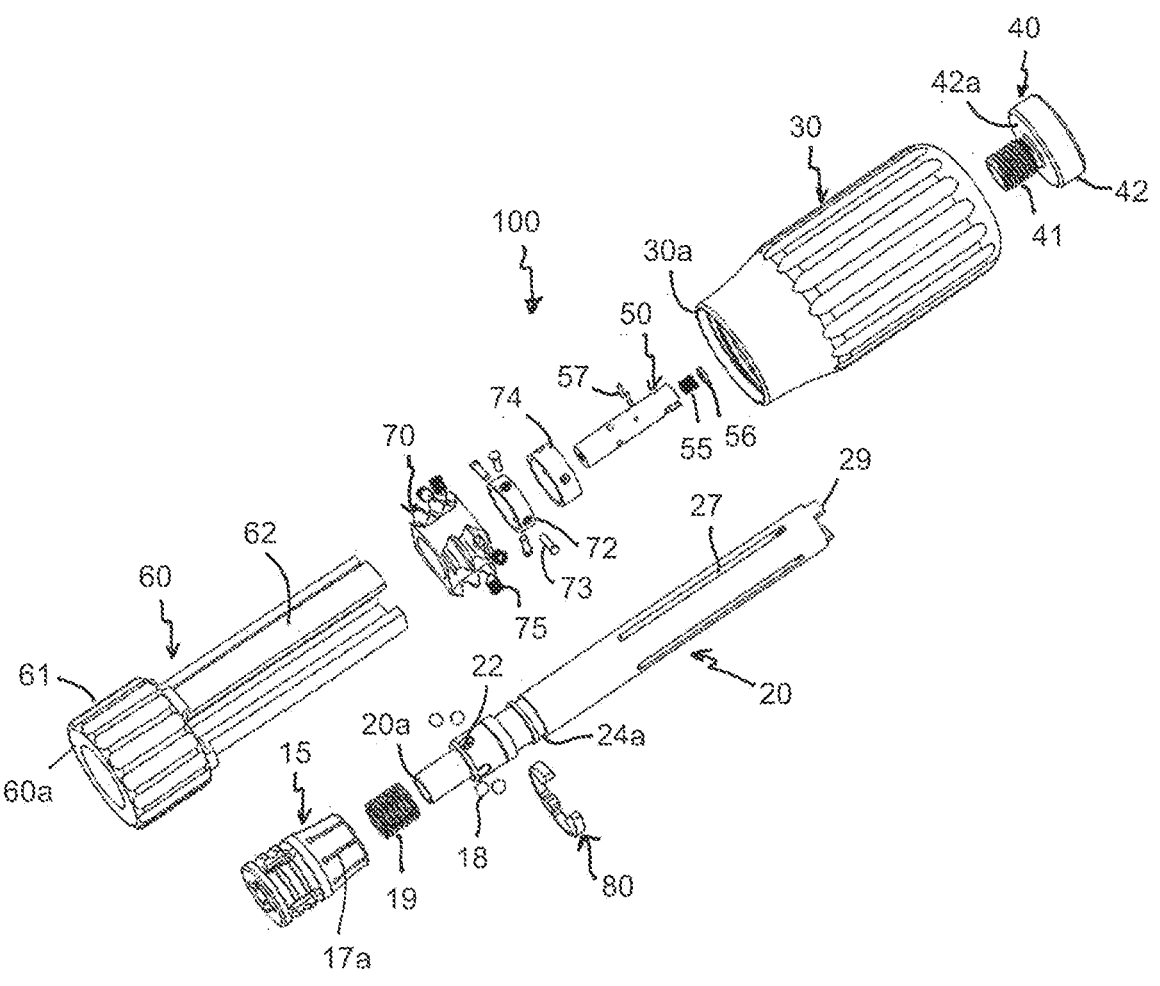
FIG. 3 shows a perspective exploded view of the instrument shown in FIGS. 1 and 2.

Referring additionally to FIGS. 8 to 10, the hollow shaft 20 is an elongate, substantially cylindrical part which has a front end 20a and a rear end 20b. The front end 20a faces towards the shank inserter 10 when assembled with the shank inserter. Moreover, the hollow shaft 20 has a channel extending through the hollow shaft from the front end to the rear end, such that the needle 4 can extend fully therethrough. The channel has various sections described below. Adjacent to the front end 20a, there is a connection portion 21 for connecting the hollow shaft 20 to the coupling portion 15. The connection portion has, at an outermost end, a hollow cylindrical section 21a with an outer diameter such that the cylindrical section 21a is configured to be received in the coupling portion 15, and with an inner diameter sized to receive a portion of the drive shaft 11 behind the groove 12a (FIG. 1). Adjacent to the cylindrical section 21a, there is a section 21b with a greater outer diameter, so that a first step 21c is formed therebetween. The first step 21c may serve as an abutment for a spring of the connection portion 15. The section 21b has, close to the step 21c, several equidistantly distributed circumferential compartments 22 for engagement members, such as balls 18, that are configured to engage the groove 12a of the drive shaft 11 and axially hold the drive shaft 11 while allowing rotation of the drive shaft. At a side of the compartments 22 closer to the rear end 20b, a receiving section 23 for receiving the connection portion 12 of the drive shaft is formed that has an inner contour corresponding to the outer contour of the connection portion so as to provide a form-fit connection between the drive shaft 11 and the hollow shaft 20. Preferably, the receiving section 23 has a standard connection contour such as a quarter inch female square contour. Behind the connection portion 21, the hollow shaft 20 has a length with a slightly reduced outer diameter, so that a second step 21d is formed that serves for engagement with the connection portion 15. At a distance from the second step 21d, a circumferential projection 24 is provided, such that between this projection 24 and a following increased diameter section, a groove 24a is formed that is configured to receive a circlip or tension ring 80 (FIG. 3).

Figure 5:
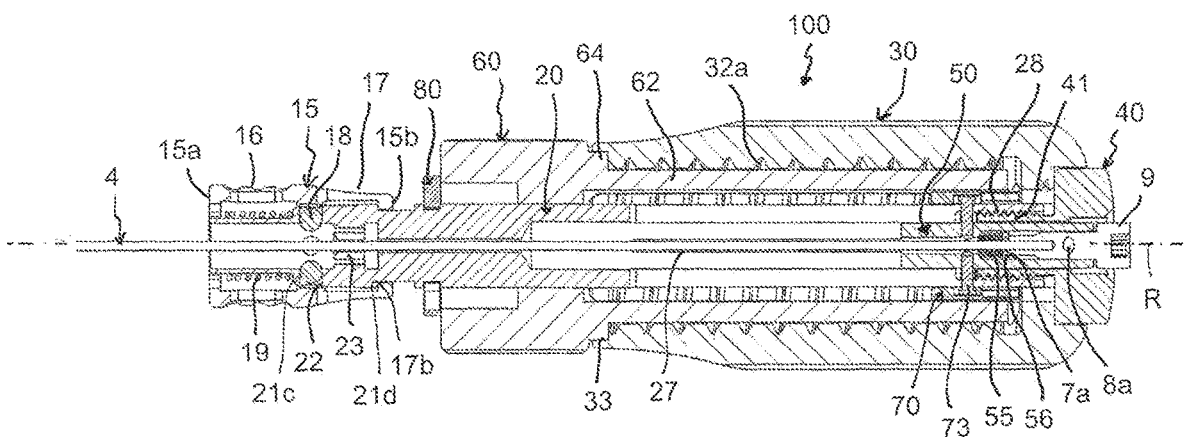
FIG. 5 shows a cross-sectional view of the instrument of FIGS. 3 and 4 with a needle inserted therein, the cross-section taken in a plane including an axis of rotation of a handle portion and an actuator of the instrument, wherein a needle holder is in a retracted or rearmost position.
Figure 6:
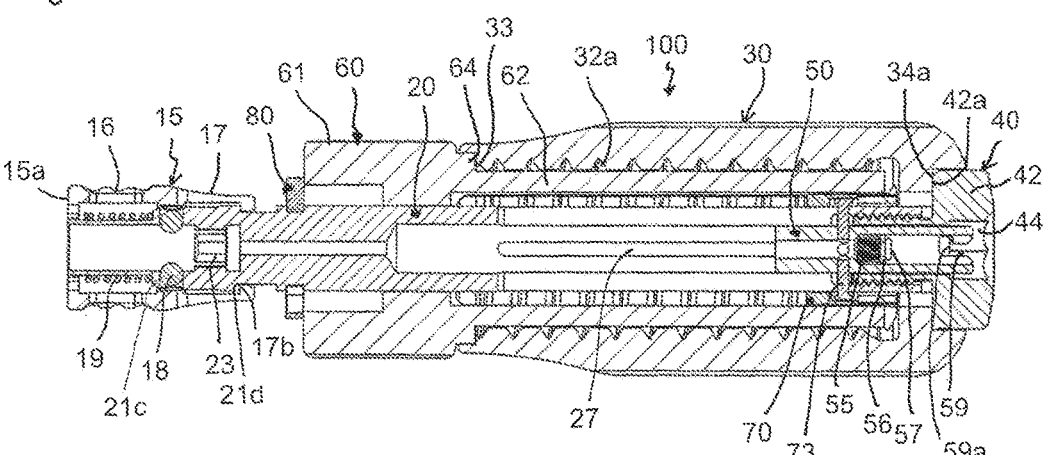
FIG. 6 shows the cross-sectional view of FIG. 5 without the needle.

Adjacent to the receiving section 23 towards the rear end 20b, a narrowed section 25 of the channel may have a width that is only slightly greater than an outer diameter of the needle 4. This may provide guidance of the needle 4 once the needle extends through the hollow shaft 20. The channel then widens towards the rear end into a cylindrical needle holder receiving section 26, which serves for receiving the needle holder 50 therein. The needle holder receiving section 26 has a length such that the needle holder 50 can move therein in an axial direction along a defined length. At least one, preferably four, axially elongate slots 27 which are closed at both ends are formed in the wall of the hollow shaft 20 equidistantly from one another in the circumferential direction. The slots 27 permit pins 73 to extend therethrough for holding the needle holder 50, as explained in greater detail below. With the slots 27, the distance which the needle holder 50 can travel within the hollow shaft 20 is defined. The position of the slots 27 in the axial direction is such that when the pins 73 abut front ends of the slots 27 towards the front end 20a of the hollow shaft, respectively, the needle holder 50 is in a foremost position (FIG. 7), and when the pins abut against opposite rear ends of the slots 27, respectively, the needle holder 50 is at a rearmost position (FIGS. 5 and 6).

Adjacent to the rear end 20b, an internal thread 28 is formed in the hollow shaft 20 that is configured to cooperate with an external thread 41 on a shaft of the fixation member 40 (FIGS. 3 to 7). In addition, two projections 29 that are offset by 180° extend from the rear end 20b in a direction away from the front end 20a. The projections 29 are configured to cooperate with corresponding recesses in the handle portion 30 to provide a form-fit connection between the hollow shaft 20 and the handle portion 30. Thereby, rotation of the hollow shaft 20 relative to the handle portion 30 is prevented when the fixation member 40 is screwed into the hollow shaft. It shall be noted that other rotation preventing structures between the hollow shaft 20 and the handle portion 30 may also be envisaged.

Figure 4:
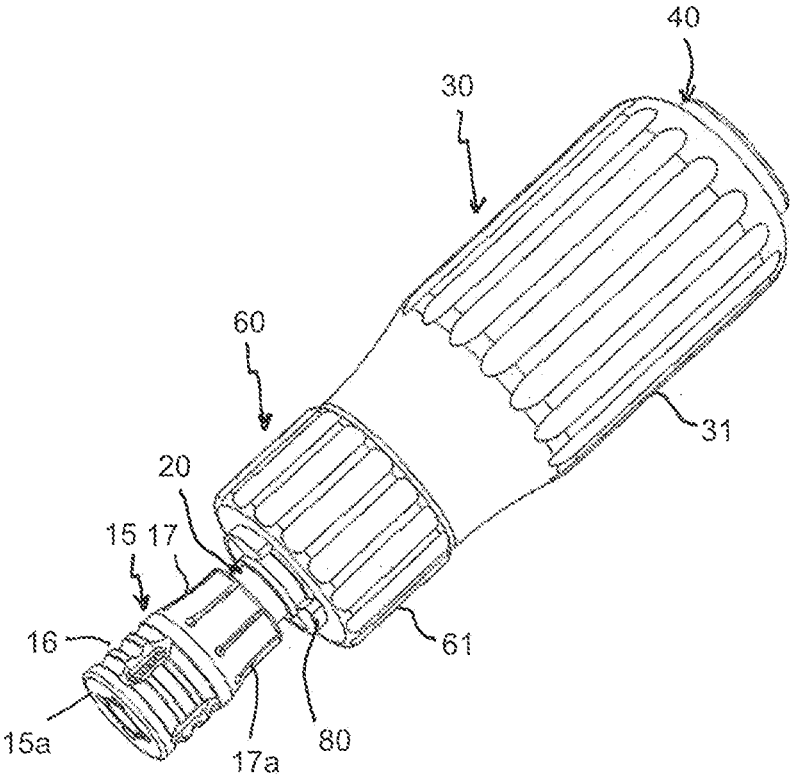
FIG. 4 shows a perspective view of the instrument of FIG. 3 in an assembled state.

In the following, the coupling portion 15 which couples the hollow shaft 20 to the drive shaft 11 will be described in greater detail. The coupling portion 15 is exemplary, and any other suitable coupling can also be used. As best seen in FIGS. 3 to 7, the coupling portion 15 is a sleeve-like part configured to receive a portion of the hollow shaft 20 therein. The coupling portion has a front section 16 adjacent a front end 15a and a rear section 17 adjacent a rear end 15b. The front section 16 is configured to receive the cylindrical section 21a of the hollow shaft 20 therein, and the rear section 17 is configured to receive the receiving section 23 of the hollow shaft therein that cooperates with the connection portion 12 of the drive shaft 11. The rear section 17 is flexible, for example, by means of slits 17a, as best seen in FIGS. 3 and 4, that are open to the rear end 15b. The slits 17a and an inner annular projection 17b at the rear end 15b enable the rear section 17 of the coupling portion 15 to be snapped over the portion 21b of the hollow shaft 20 and engage the hollow shaft at the second step 21d. At a distance from the rear end 15b, balls 18 are provided that extend radially to some extent through the compartments 22 in the hollow shaft 20. In the front section 16, a helical spring 19 is housed in a compartment. The helical spring 19 extends around the portion 21a of the hollow shaft 20 and abuts against the first step 21c of the hollow shaft 20. By means of this, the hollow shaft 20 is biased against the inner annular projection 17b, so that the hollow shaft is firmly connected to the coupling portion. When the coupling portion is detached from the drive shaft 11, the balls 18 are moved out of the groove 12a and remain in recesses of the coupling portion 15.

Turning now in addition to FIGS. 11 to 14, the handle portion 30 will be described in greater detail. The handle portion may be an elongate, substantially cylindrical part that has a front end 30a and a rear end 30b. An outer surface portion 31 that extends from a position close to the rear end 30b to a distance from the front end 30a includes a gripping structure such as, for example, axial grooves. Between the outer surface portion 31 with the gripping structure and the front end, the outer diameter of the handle portion may taper to substantially match an outer diameter of a portion of the actuator 60. The handle portion 30 also has a cylindrical bore 32 extending from the front end 30a to a distance from the rear end 30b, which is provided with an internal thread 32a. Preferably, the pitch of the internal thread 32a corresponds to a pitch of the bone thread of the bone anchor 1. Also preferably, a direction of the internal thread 32a is the same as a direction of the bone thread of the bone anchor 1. An inner diameter of the bore 32 is such that the hollow shaft 20 and a portion of the actuator 60 can extend therein, and the transmission member 70 which acts between the needle holder 50 and the handle portion 30 can engage the internal thread 32a.

Figure 7:
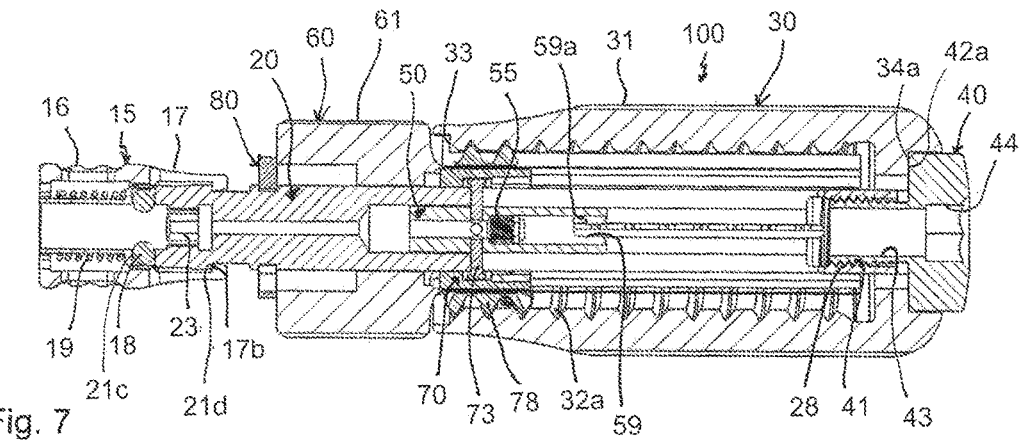
FIG. 7 shows the cross-sectional view of FIG. 6, wherein the needle holder is in an advanced or foremost position.
Figures 11, 12, 13, 14:
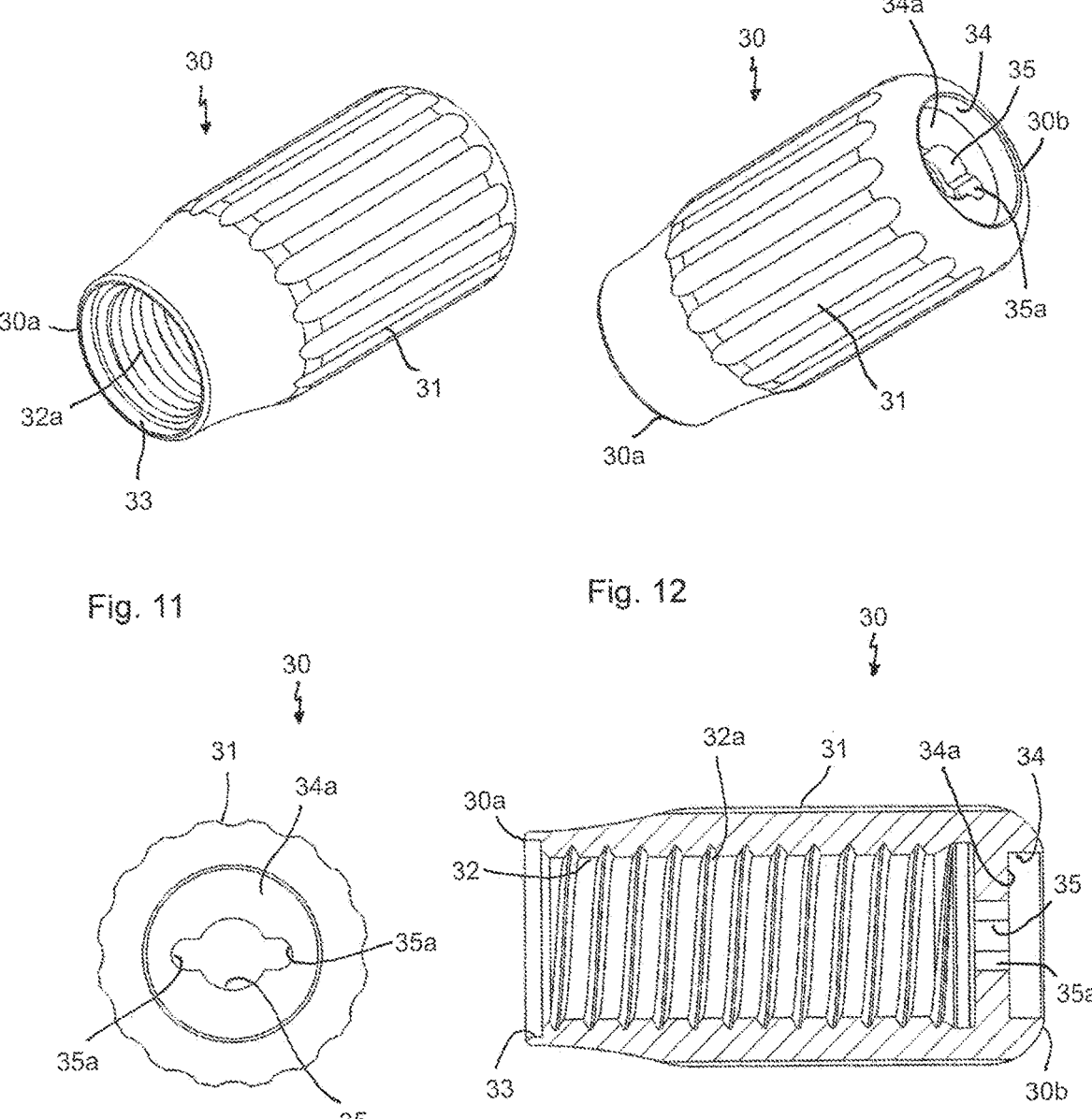
FIG. 11 shows a perspective view from a front end of the handle portion of the instrument of FIGS. 3 to 7.
FIG. 12 shows a perspective view from a rear end of the handle portion of FIG. 11.
FIG. 13 shows a rear view of the handle portion of FIGS. 11 and 12.
FIG. 14 shows a cross-sectional view of the handle portion of FIGS. 11 to 13, the cross-section taken in a plane including a central longitudinal axis of the handle portion.

At a distance from the front end 30a, there may be a short cylindrical section 33 with an inner diameter that is greater than the inner diameter of the thread 32a and that may serve for receiving a portion of the actuator 60 therein. Adjacent to the rear end 30b, a cylindrical recess 34 is formed that is sized to receive a cylindrical head 42 of the fixation member (FIGS. 5 to 7). Between the end of the bore and the cylindrical section 34, a coaxial channel 35 with a reduced inner diameter compared to the diameter of the bore 32 and compared to the cylindrical section 34 is formed, and that further has two rounded side recesses 35a offset by 180° that are configured to receive the projections 29 of the hollow shaft 20 in order to connect the hollow shaft 20 and the handle portion in an rotationally secured manner against each other.

As further depicted in FIGS. 5 to 7, the fixation member 40 has a channel 43 with an inner diameter such that the needle holder 50 can extend therein when the needle holder 50 is in the rearmost position. This allows insertion and/or removal of the needle 4 through the fixation member 40. Moreover the fixation member 40 has a tool engagement recess 44 in the head 42 for screwing the fixation member into the threaded section 28 of the hollow shaft 20. The underside 42a of the head 42 of the fixation member is configured to abut against the bottom 34a of the recess 34 in the handle portion 30 (FIGS. 6 and 7) to firmly connect the hollow shaft 20 and the handle portion 30 when the fixation member 40 is tightened.

Figure 15:
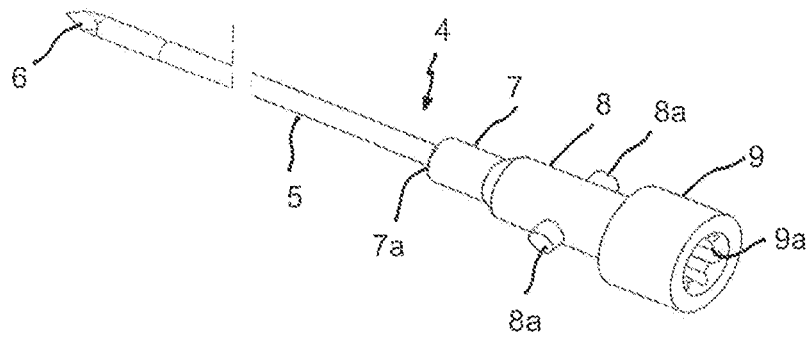
FIG. 15 shows an enlarged perspective view from a rear end of a needle to be used with the instrument of FIGS. 3 to 7.
Figure 16:
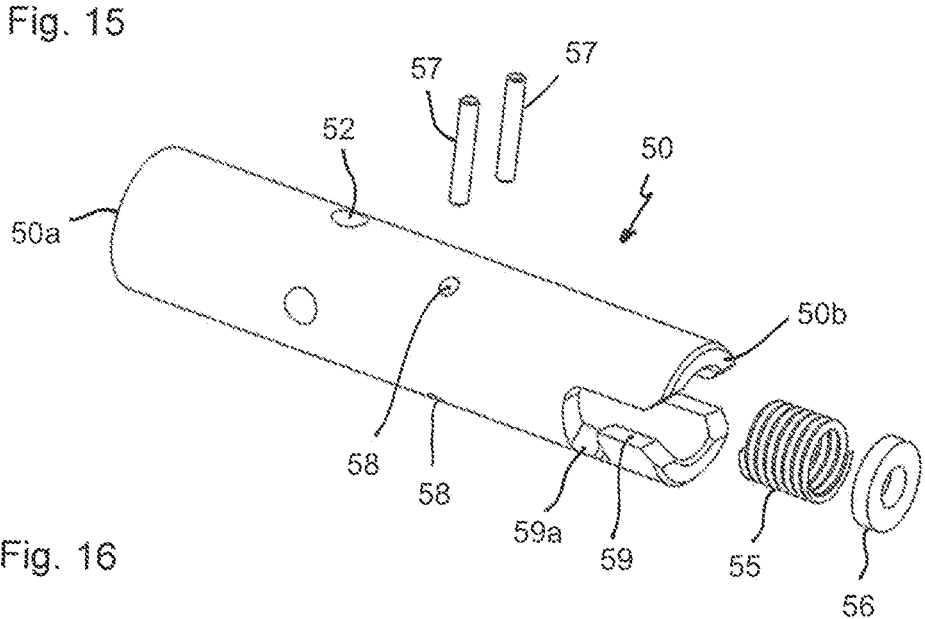
FIG. 16 shows a perspective exploded view of the needle holder of the instrument of FIGS. 3 to 7.
Figure 17:
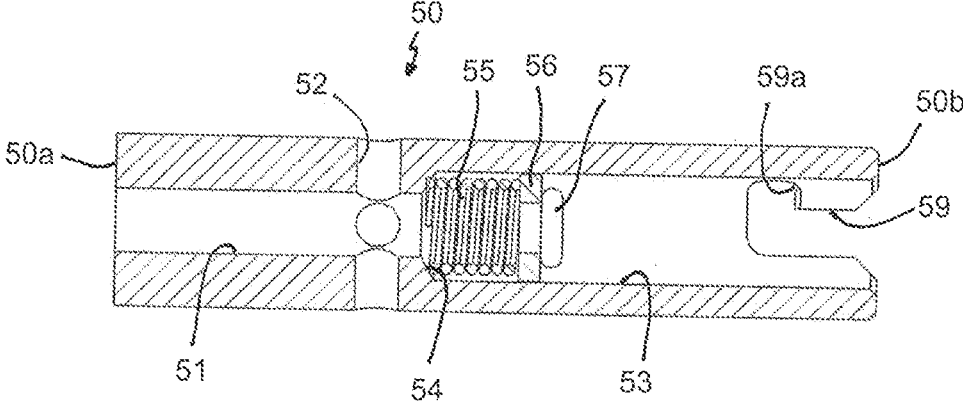
FIG. 17 shows a cross-sectional view of the needle holder of FIG. 16 in an assembled state, the cross-section taken in a plane including a central longitudinal axis of the needle holder.

Referring in addition to FIGS. 15 to 17, the needle 4 and the needle holder 50 will be described in greater detail.

As depicted in FIG. 15, the needle 4 includes a thin rod portion 5 with a tip 6 at a front end. The tip 6 preferably is a sharp tip that is suitable for picking a hole into bone. At a side opposite to the tip 6, a holding portion is provided that includes a cylindrical front portion 7, an intermediate thicker portion 8, and a head portion 9 at a rear end. Between the rod portion 5 and the cylindrical front portion 7, a small shoulder 7a is formed. At an outer surface of the intermediate portion 8, two projections 8a, preferably cylindrical projections, extend outward in opposite directions. The projections 8a serve for mounting the needle 4 to the needle holder 50. The head portion 9 includes an engagement portion 9a for a tool at its free end. With the tool, such as a driver, the needle 4 can be pushed and rotated to mount and release the needle from the needle holder 50. It shall be noted that the needle can be any suitable needle, such as a Jamshidi needle or a needle having a special tip, such as a tip provided with a sensor.

The needle holder 50 is a substantially cylindrical part with a front end 50a and a rear end 50b. The needle holder has a channel extending completely through the needle holder from the front end 50a to the rear end 50b, such that the needle 4 can be inserted from the rear end 50b with the tip 6 and can extend with the rod portion 5 all through the needle holder 50. Adjacent to the front end 50a, the channel has a front section 51 with an inner diameter large enough to guide the rod portion 5 of the needle 4 therethrough. At a distance from the front end 50a, four transverse through holes 52 are formed equidistantly in the circumferential direction in the wall of the needle holder 50. The through holes 52 are configured to receive pins 73 (FIGS. 5 to 7) therethrough to connect the transmission member 70 with the needle holder 50, as explained further below. Adjacent to the rear end 50b, a receiving section 53 for the holding portion of the needle 4 is provided that has a greater inner diameter than the channel of the front portion 51. At the transition between the receiving section 53 and the front section 51, the inner diameter of the channel decreases towards the front section 51, whereby a shoulder 54 is formed that serves as an abutment for a helical spring 55 arranged in the receiving section 53. The helical spring 55 biases a washer 56 against pins 57 that extend through pairs of holes 58, respectively. In greater detail, each pin 57 extends through two holes 58 in the wall of the needle holder. More specifically, the holes 58 are offset in a circumferential and in the axial direction from the holes 52, and the inserted pins 57 extend transverse to the longitudinal direction but at a radial distance from the central longitudinal axis. A distance of the pins 57 from each other is such that the rod portion 5 of the needle can extend therethrough without being hindered. The pins 57 prevent falling out of the washer 56 through the rear end 50b if no needle is inside the needle holder 50.

At the rear end 50b, two axially extending recesses 59 that are offset by 180° from each other are formed in the wall of the needle holder 50 that permit the projections 8a of the holding portion of the needle 4 to be guided therethrough when the needle 4 is inserted. At a distance from the rear end 50b, the recesses 59 continue into end portions 59a which extend in the circumferential direction, and thus are transverse to the axially extending portions of recesses 59. The end portions 59a extend circumferentially in a same direction of revolution so that, when the projections 8a reach the end portions during insertion of the needle 4, rotation in one direction moves the projections into the end portions 59a of the recesses 59, respectively, and rotation in the other direction moves the projections out of the end portions 59a.

When the projections 8*a* are received in the end portions 59*a*, the needle 4 is secured against inadvertent removal from the needle holder 50. An outer diameter of the cylindrical front portion 7 of the holding portion of the needle 4 is greater than an inner diameter of the washer 56. As a result, when the shoulder 7*a* of the front portion 7 abuts against the washer 56, the spring 55 urges the washer against the shoulder 7*a*, so that the needle 4 as a whole is biased in a direction towards the rear end 50*b* of the needle holder 50. Thereby, the projections 8*a* are held in the transverse end portions 59*a* of the axial recesses 59. Removal of the needle 4 can be accomplished by pushing the rear portion of the needle against the washer 56, which frees the projections 8*a* so that they can be moved out of the transverse end portions 59*a* by rotating the needle in a counter or opposite direction. For example, in the embodiment, the end portions 59*a* extend in a counterclockwise direction, so that pushing and rotating the needle in the counterclockwise direction locks the needle 4 in the needle holder 50, while pushing and rotating the needle in the clockwise direction releases the needle 4 from the needle holder 50. This push and turn action allows for quick and simple mounting and removal of the needle from the needle holder.

Figures 18, 19, 20:
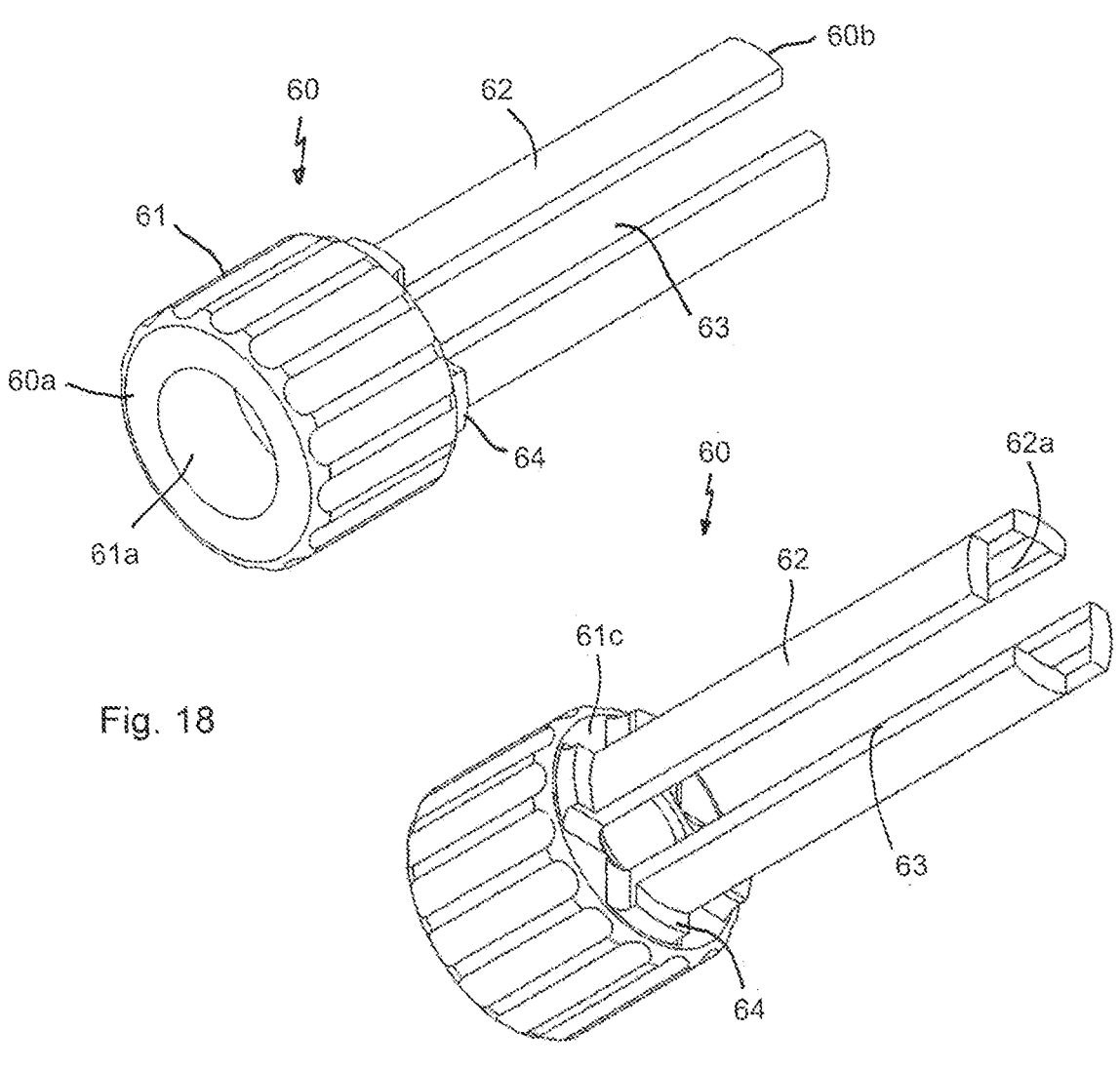
FIG. 18 shows a perspective view from a front end of the actuator of the instrument of FIGS. 3 to 7 for actuating the movement of the needle holder relative to the handle portion.
FIG. 19 shows a perspective view from a rear end of the actuator of FIG. 18.
FIG. 20 shows a cross-sectional view of the actuator of FIGS. 18 and 19, the cross-section taken in a plane including a central longitudinal axis of the actuator.

Referring additionally to FIGS. 18 to 20, the actuator 60 will be described. The actuator 60 has a front end 60*a* and a rear end 60*b*. Adjacent to the front end 60*a*, a substantially cylindrical gripping portion 61 is formed that has a gripping structure such as axially extending grooves at its outer surface. A passage extends completely through the gripping portion 61 and includes a first cylindrical coaxial bore 61*a* adjacent the front end 60*a* followed by a second cylindrical coaxial bore 61*b*. The second cylindrical bore 61*b* has an inner diameter that allows guiding of the hollow shaft 20 therethrough. More specifically, when the instrument is assembled, the groove 24*a* of the hollow shaft 20 is located at the front end 60*a* of the actuator 60. A rear end surface 61*c* of the gripping portion 61 faces towards the front end 30*a* of the handle portion 30 in the assembled state. From the end surface 61*c* of the gripping portion 61, four equidistantly spaced posts 62 protrude away from the free end surface to form the rear end 60*b* of the actuator 60. The posts 62 have a cylindrical outer surface and a substantially flat inner surface portion 62*a*. The gaps or slots 63 between the posts 62 form a guiding structure for the transmission member 70. Adjacent to the gripping portion 61, the posts 62 have foot portions 64 which join the posts with the gripping portion 61. An outer contour of the foot portions 64 is also cylindrical, with an outer diameter slightly smaller than an outer diameter of the gripping portion 61. The posts 62 protrude from an innermost side of the foot portions 64, respectively. An outer diameter of the actuator 60 in the region of the posts 62 is smaller than an inner diameter of the threaded bore 32 of the handle portion 30, such that the posts 62 can extend into the bore 32 and leave sufficient space for the transmission member 70 to extend partially into that space. In the assembled state, the foot portions 64 can extend into the widened cylindrical recess 33 adjacent the front end 30*a* of the handle portion 30, as shown in FIGS. 5 and 6. Moreover, in the assembled state, when the posts 62 extend into the bore 32 of the handle portion 30, as shown in FIGS. 5 to 7, the rear end 60*b* of the actuator 60 extends beyond the internal thread 32*a* of the handle portion 30 towards the rear end 30*b* of the handle portion. This permits full use of the thread 32*a* for the travel of the transmission member 70. An inner diameter of the actuator 60 in the region of the posts 62 is such that the hollow shaft 20 can extend therethrough.

Figures 21, 22, 23:
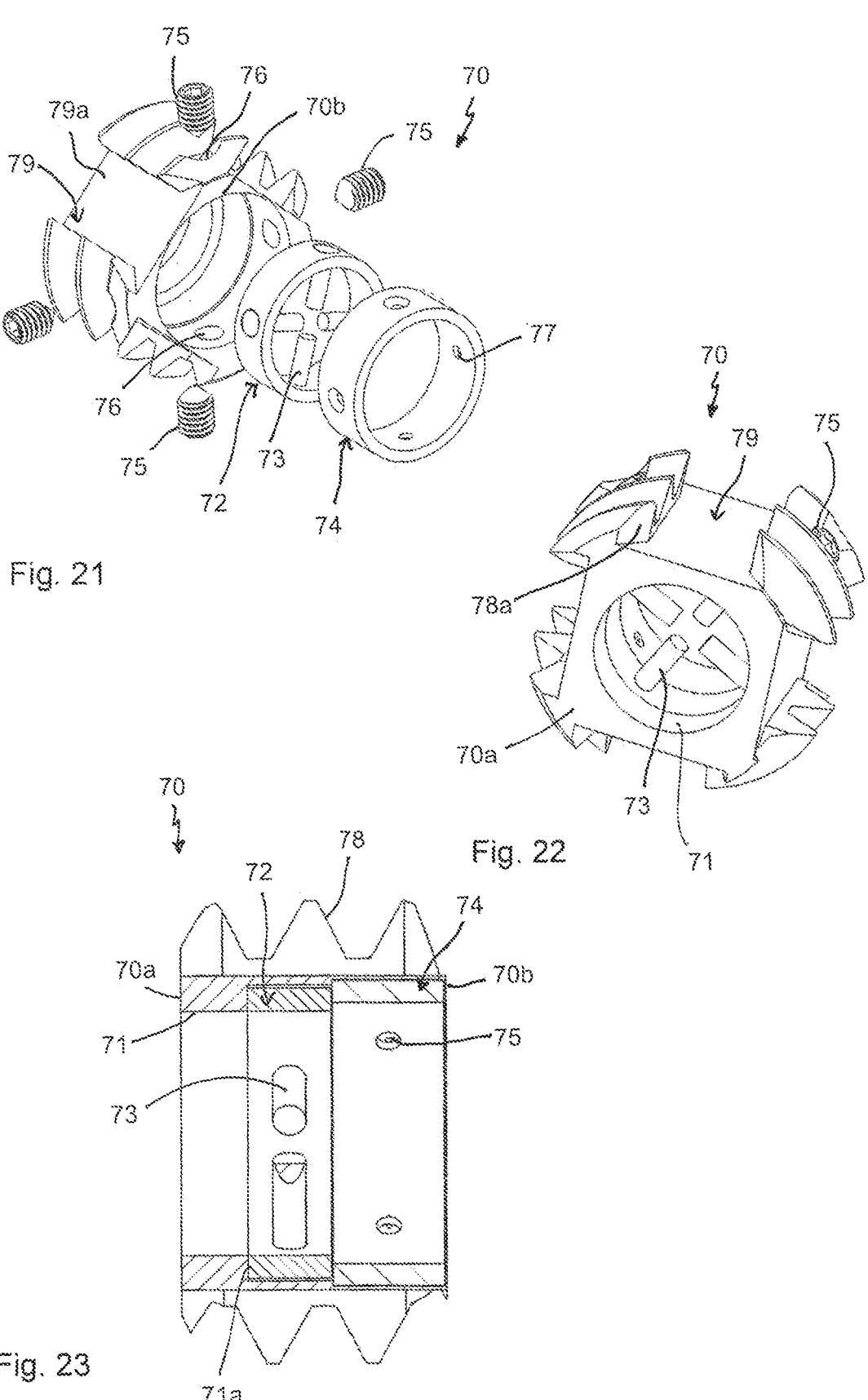
FIG. 21 shows a perspective exploded view of a transmission member of the instrument of FIGS. 3 to 7.
FIG. 22 shows a perspective view from a front end of the transmission member of FIG. 21 in an assembled state.
FIG. 23 shows a cross-sectional view of the transmission member of FIGS. 21 and 22, the cross-section taken in a plane including a central longitudinal axis of the transmission member.

Turning to FIGS. 21 to 23, the transmission member 70 will be described in greater detail. The transmission member 70 is a sleeve-like part with a front end 70*a* and a rear end 70*b*. An inner passage 71 of the sleeve is sized such that the transition member 70 fits around the hollow shaft 20, preferably with only enough radial play to allow the transition member 70 to move easily along the hollow shaft 20. At a distance from the front end 70*a*, a first ring member 72 is arranged in which the pins 73 mentioned above are mounted. Four pins 73 are provided that extend inwards in a radial direction and that are 90° offset from each other in the circumferential direction. The pins 73 have a length such that they can extend through the slots 27 on the hollow shaft 20 into the transverse holes 52 of the needle holder 50, to connect the needle holder 50 to the transmission member 70 without obstructing the needle 4 when the needle extends through the needle holder 50. The first ring member 72 is rotatable in the transmission member 70. The first ring member is secured to the transmission member 70 against escaping through the front end 70*a* by a step 71*a* in a wall of the passage 71. In addition, the first ring member is secured against escaping through the rear end 70*b* by a second ring member 74 that has an inner diameter such that the second ring member abuts in a mounted state against the first ring member 72. The second ring member 74 is fixed to the transmission member 70 via set screws 75 that engage threaded transverse holes 76 in the transmission member 70 and corresponding threadless holes 77 in the second ring member 74.

The outer surface of the transmission member 70 includes an external thread 78 that is configured to cooperate with the internal thread 32*a* of the handle portion 30. Four axial cutouts 79 with a substantially flat bottom 79*a* are provided in the external surface of the transmission member 70. The cutouts 79 are 90° offset from each other and have a width such that the posts 62 can extend into the cutouts 79 and are guided therein. The substantially flat inner surface portion 62*a* of the posts 62 can slide on the flat bottom 79*a* of the cutouts 79. At the front end 70*a*, the external thread 78 may have beveled portions 78*a* at the borders of the slots 79 to facilitate insertion of the posts 62. When the transmission member 70 is mounted to the actuator 60, the thread 78 extends into the slots 63 between the posts 62 of the actuator 60. The axial length of the transmission member 70 may be at least one, and preferably at least two turns of the thread 78. When the transmission member 70 moves from the foot portion 64 of the posts 62 until the rear end of the threaded bore 32*a* in the handle portion 30, the needle holder 50 travels along a distance that corresponds to the axial length of the slots 27 in the hollow shaft 20.

The parts and portions of the instrument and/or the bone anchor insertion device, the bone anchor, and/or the needle may be made of any material, preferably, however, of a bio-compatible material, such as titanium or stainless steel, or of any other bio-compatible metal or metal alloy, or a bio-compatible plastic material. For a bio-compatible alloy, a NiTi-alloy, for example Nitinol, may be used. Other materials that can be used may be Magnesium or Magnesium alloys, bio-compatible plastic materials that can be used may be, for example, Polyether ether ketone (PEEK) or Poly-L-lactide acid (PLLA). The parts can be made of the same or of different materials from one another. For the instrument, a material that is more easy to clean may be preferred.

The needle holder 50, the hollow shaft 20, the transmission member 70, the handle portion 30, and the actuator 60 are usually preassembled such that their respective front ends face the direction of the connection portion 15. The transmission member 70 is arranged around the hollow shaft so that the pins 73 that extend inwardly from the first ring member 72 extend through the slots 27 of the hollow shaft 20 into the transverse holes 52 of the needle holder 50. The actuator 60 is placed with the gripping portion 61 around the hollow shaft 20 such that the posts 62 engage the cutouts 79 in the outer surface of the transmission member 70. The handle portion 30 is screwed onto the transmission member 70, and the hollow shaft 20 is fixed to the handle portion 30 via the fixation member 40 that is screwed from the rear end 30b of the handle portion 30 into the thread 28 of the hollow shaft 20. The circlip 80 is placed into the groove 24a and forms an abutment for the front end 60a of the actuator 60. Tightening the fixation member 40 firmly fixes the hollow shaft 20 to the handle 30 so that rotation of the handle 30 also rotates the hollow shaft 20. The actuator is rotatable with respect to the hollow shaft 20 and with respect to the handle portion 30.

In operation, when the actuator 60 is rotated, the rotational movement of the posts 62 forces the transmission member 70 to travel in the axial direction via the engagement of the thread 78 of the transmission member 70 and the thread 32a of the handle portion 30. Since the transmission member 70 is connected via the pins 73 to the needle holder 50, the needle holder 50 will travel axially together with the transmission member 70. When the pins 73 abut against the front end of the slots 27, the needle holder 50 is at its foremost or advanced position as shown in FIG. 7, and the tip 6 of an inserted needle 4 can assume its greatest distance from the tip 3 of the bone anchor. When the pins 73 abut against the rearward end of the slots 27 in the hollow shaft 20 as depicted in FIGS. 5 and 6, the tip 6 of an inserted needle is at its rearmost or retracted position.

To use the instrument 100 with a shank inserter 10, the coupling portion 15 is mounted to the connection portion 21 of the hollow shaft by snapping the rear section 17 of the coupling portion 15 over the connection portion 21 so that the second step 21d is engaged by the inner annular rim 17b of the connection portion 15, as shown in FIGS. 5 to 7.

The instrument 100 preassembled in this manner can be connected to a shank inserter 10. To accomplish this, the connection portion 12 of the drive shaft 11 is inserted into the connection portion 21 of the hollow shaft and is received in the receiving section 23, so that the form-fit engagement allows transmission of torque to the drive shaft 11.

The shank inserter may already be connected to a bone anchor 1 to be inserted into bone, or the bone anchor 1 can be fixed to the instrument when the shank inserter has already been connected to the instrument 100.

In a next step, the needle 4 can be inserted. To accomplish this, the needle holder 50 is moved by rotating the actuator in the counter-clockwise direction until the needle holder 50 is in the rearmost position as shown in FIGS. 5 and 6. Then, the needle 4 is inserted through the fixation member 40 and guided with the tip 6 and the rod portion 5 fully through instrument 100 and the shank inserter until the tip 6 protrudes out of the shank 2 of the bone anchor 1. The needle 4 is fixed to the needle holder 50 by a push and turn action to move the projections 8a into the end portions 59a of the axial recesses 59. Removal of the needle 4 can be accomplished by pushing and rotating the needle in the other direction.

Referring to FIGS. 24a to 24d, in clinical use, first, the instrument 100 is coupled to the shank inserter 10. The shank inserter 10 may be already attached to a bone anchor 1. The needle 4 is inserted and locked in the needle holder.

By rotating the actuator 60 in the clockwise direction, the needle 4 is advanced to an extent such that the tip 6 of the needle 4 projects to a desired distance out of the tip 3 of the bone anchor 1. The position of the needle 4 can be adjusted in a stepless manner.

Figures 24A, 24B, 24C, 24D:
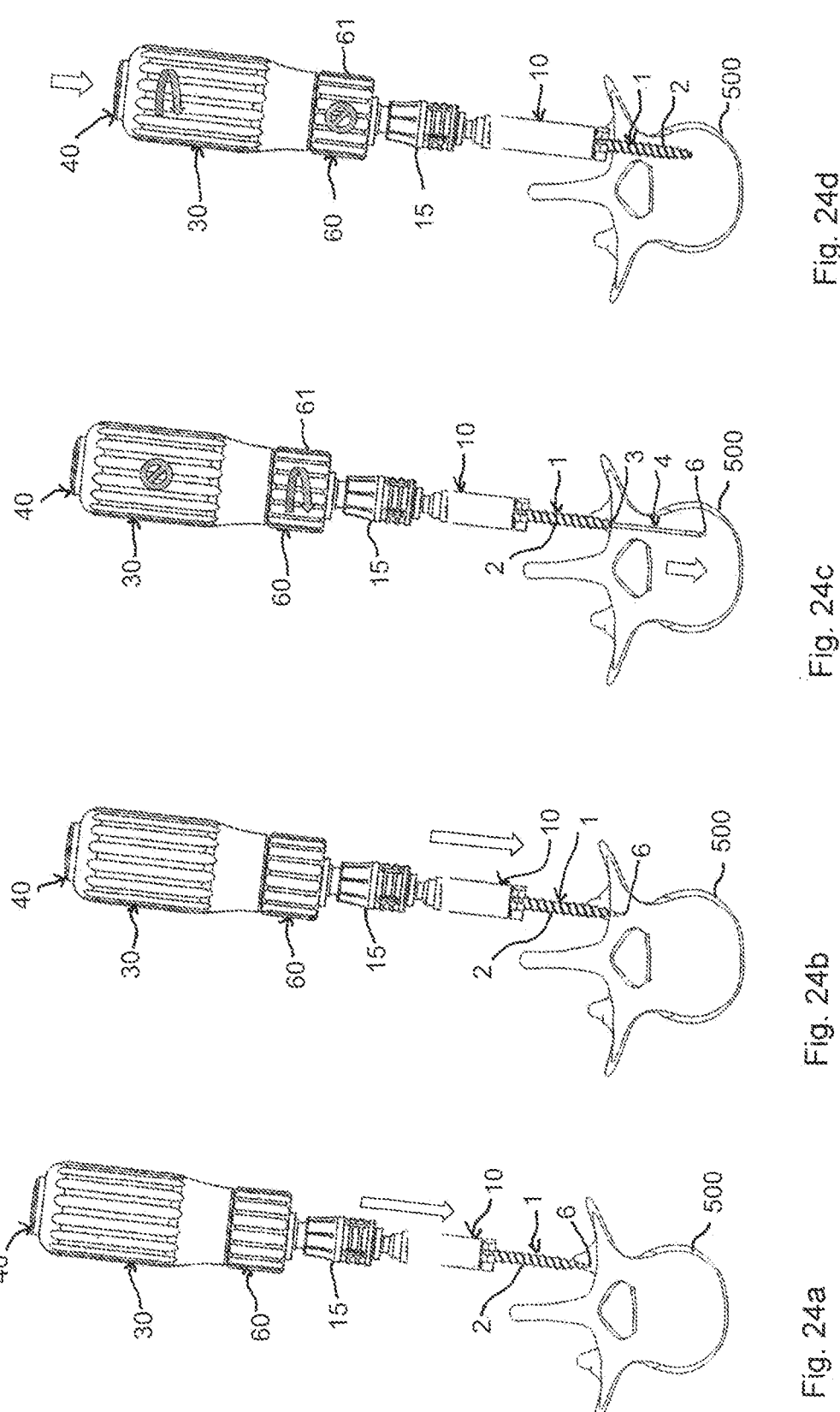
FIGS. 24a to 24d show schematic views of steps of use of the instrument of FIGS. 3 to 7 together with an insertion device for a bone anchor.

As shown in FIG. 24a, a surgical instrument prepared in this manner is ready to insert the attached bone anchor 1 into bone, in the example, in the pedicle of a vertebra 500. Next, as shown in FIG. 24b, the bone anchor is placed onto the bone surface and the tip 6 of the needle 4 is hit into the bone until the needle has penetrated the cortical bone.

Next, as depicted in FIG. 24c, the handle portion 30 is held stationary and the actuator 60 is rotated by gripping and rotating the gripping portion 61 in the clockwise direction. Thereby, the needle 4 penetrates deeper into the bone.

As further shown in FIG. 24d, once the desired depth has been reached, the gripping portion 61 of the actuator 60 is held stationary and the handle portion 30 is rotated in the clockwise direction to screw the bone anchor 1 over the needle 4 into the bone. Preferably, the bone anchor 1 is a self-tapping bone anchor that is configured to cut the thread into the bone by itself during rotation.

Finally, the shank inserter 10 can be decoupled from the bone anchor 1, together with the instrument 100 still attached to the shank inserter and the needle 4 still extending through the entire device. Alternatively, the needle 4 is removed first, and the shank inserter 10 is released from the bone anchor thereafter.

Since the path the needle can travel covers about a length of the shank of a usual bone anchor or more, the instrument 100 and the same needle 4 can be used in connection with different bone anchors having different lengths.

Figure 25:
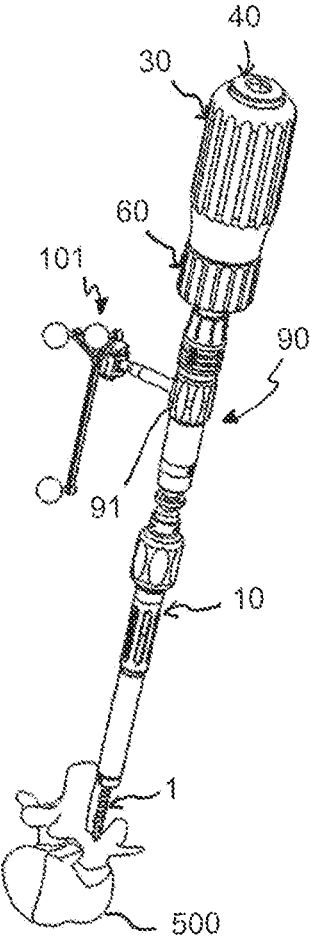
FIG. 25 shows a perspective view of a second embodiment of a combined surgical instrument which includes the instrument shown in FIGS. 1 to 24d.

Referring to FIG. 25, a second embodiment of the surgical instrument is shown. Identical or similar parts and portions are indicated with the same reference numerals, and the descriptions thereof are non-repeated. The shank inserter 10 and the instrument 100 are identical to the previous embodiment. However, between the shank inserter 10 and the instrument 100, an adapter 90 is mounted that has a rear end that is coupled to the hollow shaft 20 in the same manner as the drive shaft 11 of the previous embodiment. The adapter 90 has a front connection portion that is connected to the shank inserter 10. The hollow shaft 20 of the instrument 100 is coupled to an inner shaft (not shown) of the adapter member 90, which is also coupled to the drive shaft of the shank inserter 10. Thus, torque can be transmitted from the handle portion 30 through the adapter member 90 to the drive shaft 11 of the shank inserter 10. A secondary instrument 101, such as a navigation array that includes transmitters or receivers for electromagnetic radiation, can be mounted on the adapter member 90 via a mounting sleeve 91. The mounting sleeve 91 may be, for example, rotatable around the shaft of the adapter member 90. By means of this, while the torque is transmitted via the handle 30 to the drive shaft, the secondary instrument 101 can be kept stationary by gripping it, for example, with the user's other hand. Thereby, the orientation of the navigation array 101 is maintained relative to the navigation system. This may be used for surgery under fluoroscopy or with computer-based navigation assisted systems.

It shall be noted that, instead of a navigation array, other secondary instruments can also be used via the adapter member 90.

Further modifications of the instrument or the parts thereof may also be possible. In particular, the shapes of the various parts are not limited to the specific shapes shown in the embodiments. The instrument can also be used for inserting a syringe for injecting bone cement or other substances after or instead of a needle as shown in the embodiment. For the actuating mechanism, any suitable actuating mechanism that can convert a rotational motion of an actuator into a translational motion of the needle holder can be used. The instrument can also be used in connection with a drill instead of a shank inserter or with other suitable surgical instruments. The instrument can also be used without a needle or with needles of different types and/or with different lengths.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. An instrument for use in surgery, the instrument being connectable to a bone anchor insertion device that comprises a drive shaft configured to engage a bone anchor, the drive shaft defining a coaxial channel for receiving a needle therethrough, the instrument comprising:
a handle portion configured to be coupled to the drive shaft in a rotationally fixed manner to transmit torque to the drive shaft;
a needle holder configured to hold a needle and movable translationally in an axial direction relative to the handle portion;
an actuator rotatable relative to the handle portion; and
a transmission member connectable to the needle holder and movable translationally in the axial direction relative to the actuator and comprising a first advancement surface engageable with a second advancement surface of the handle portion to convert rotational movement of the actuator into translational movement of the needle holder relative to the handle portion for translationally advancing and retracting a needle held by the needle holder relative to the handle portion.

2. The instrument of claim 1, wherein the first advancement surface is on an outer surface of the transmission member and the second advancement surface is on an inner surface of an elongate passage of the handle portion.

3. The instrument of claim 1, wherein the first advancement surface and the second advancement surface are threads.

4. The instrument of claim 1, further comprising a hollow shaft that is directly connectable to the drive shaft, wherein at least part of the hollow shaft extends into the handle portion and at least part of the needle holder is positionable in the hollow shaft.

5. The instrument of claim 4, further comprising a fixation member configured to fixedly connect the hollow shaft to the handle portion at an end of the hollow shaft away from where the drive shaft connects.

6. The instrument of claim 5, wherein the fixation member defines a passage configured to permit at least a portion of the needle to extend therethrough.

7. The instrument of claim 1, wherein the needle holder is configured to releasably hold a needle.

8. The instrument of claim 7, wherein a held needle is removable from or adjustable relative to the needle holder without disassembling any other portion of the instrument.

9. The instrument of claim 7, wherein the needle is mountable to and removable from the needle holder via a push and turn action.

10. The instrument of claim 4, wherein the transmission member is a sleeve-like part positionable around the hollow shaft.

11. The instrument of claim 10, wherein the transmission member further comprises at least one engagement member configured to extend through and to be guided in a recess of the hollow shaft and to engage the needle holder.

12. The instrument of claim 11, wherein an axial length of the recess of the hollow shaft defines a range of translational movement of the needle holder relative to the handle portion.

13. The instrument of claim 1, wherein the actuator comprises a sleeve-like grip portion arranged around an axis of rotation of the handle portion and a guiding structure configured to extend at least partially into the handle portion to guide translational movement of the transmission member relative to the handle portion when the actuator is rotated.

14. The instrument of claim 13, wherein the guiding structure comprises at least two extension members that extend in the axial direction and that define a gap therebetween, wherein the second advancement surface of the transmission member is configured to extend through the gap to engage the first advancement surface at the handle portion.

15. A surgical instrument comprising the instrument of claim 1, and the bone anchor insertion device comprising the drive shaft.

16. The surgical instrument of claim 15, wherein the instrument comprises an end portion that is releasably connectable to an end portion of the drive shaft.

17. A system comprising the surgical instrument of claim 15 and the bone anchor, wherein the bone anchor comprises a thread having a first pitch, and wherein the first and second advancement surfaces comprise engageable threads each having the first pitch.

18. An instrument for use in surgery, the instrument being connectable to a bone anchor insertion device that comprises a drive shaft configured to engage a bone anchor, the drive shaft defining a coaxial channel for receiving a needle therethrough, the instrument comprising:
a handle portion configured to be coupled to the drive shaft in a rotationally fixed manner to transmit torque to the drive shaft;
a needle holder configured to hold a needle and movable translationally in an axial direction relative to the handle portion;
an actuator rotatable but axially fixed relative to the handle portion; and
a transmission member connectable to the needle holder and rotatable and movable translationally in the axial direction relative to the handle portion to convert rotational movement of the actuator into translational movement of the needle holder relative to the handle portion for translationally advancing and retracting a needle held by the needle holder relative to the handle portion;
wherein the transmission member comprises a first portion that is rotatable together with the actuator relative to the handle portion, and a second portion configured to hold the needle holder at a fixed rotational orientation relative to the handle portion when the actuator is rotated relative to the handle portion.

19. A method of implanting a bone anchor into bone with a surgical instrument comprising a bone anchor insertion device that comprises a drive shaft configured to engage the bone anchor, the drive shaft defining a coaxial channel for receiving a needle therethrough, and an instrument comprising a handle portion configured to be coupled to the drive shaft in a rotationally fixed manner to transmit torque to the drive shaft, a needle holder configured to hold a needle and movable translationally in an axial direction relative to the handle portion, an actuator rotatable relative to the handle portion, and a transmission member connectable to the needle holder and movable translationally in the axial direction relative to the actuator and comprising a first advancement surface engageable with a second advancement surface of the handle portion to convert rotational movement of the actuator into translational movement of the needle holder relative to the handle portion for translationally advancing and retracting a needle held by the needle holder relative to the handle portion, the method comprising:

advancing a bone anchor to the bone while the bone anchor is engaged by the bone anchor insertion device and the bone anchor insertion device is connected to the instrument and when a needle is held by the needle holder and extends distally past a tip of the bone anchor;

rotating the actuator while holding a rotational orientation of the handle portion to advance the needle into the bone while maintaining an axial position of the bone anchor;

rotating the handle portion while holding a rotational orientation of the actuator to advance the bone anchor over the needle into the bone while maintaining an axial position of the needle; and detaching the bone anchor insertion device and the needle from the bone anchor.

20. The method of claim 19, wherein a held needle is removable from or adjustable relative to the needle holder without disassembling any other portion of the instrument.

21. The method of claim 19, wherein a held needle is removable from or adjustable relative to the needle holder while the bone anchor insertion device remains connected to the instrument and while the bone anchor remains engaged by the bone anchor insertion device.

\* \* \* \* \*